(12) United States Patent
Yu et al.

(10) Patent No.: US 10,881,367 B2
(45) Date of Patent: Jan. 5, 2021

(54) DETECTOR MODULE, DETECTOR AND MEDICAL DEVICE

(71) Applicant: Neusoft Medical Systems Co., Ltd., Liaoning (CN)

(72) Inventors: Jun Yu, Liaoning (CN); Shuangxue Li, Liaoning (CN); Shanshan Lou, Liaoning (CN)

(73) Assignee: Neusoft Medical Systems Co., Ltd., Liaoning (CN)

( * ) Notice: Subject to any disclaimer, the term of this patent is extended or adjusted under 35 U.S.C. 154(b) by 0 days.

(21) Appl. No.: 16/458,959

(22) Filed: Jul. 1, 2019

(65) Prior Publication Data
US 2020/0000422 A1    Jan. 2, 2020

(30) Foreign Application Priority Data
Jun. 29, 2018   (CN) .......................... 2018 1 0712864

(51) Int. Cl.
*A61B 6/03*   (2006.01)
*A61B 6/00*   (2006.01)
*G01T 1/16*   (2006.01)

(52) U.S. Cl.
CPC ............ *A61B 6/4429* (2013.01); *A61B 6/032* (2013.01); *A61B 6/4266* (2013.01); *G01T 1/16* (2013.01)

(58) Field of Classification Search
CPC ........... A61B 6/027; A61B 6/032; A61B 5/02; A61B 6/02; A61B 6/03; A61B 6/42;
(Continued)

(56) References Cited

U.S. PATENT DOCUMENTS 5,912,938 A * 6/1999 Dobbs ................ G01N 23/046
378/19
8,204,171 B2 6/2012 Ikhlef
(Continued)

FOREIGN PATENT DOCUMENTS

CN   102440794 A   5/2012
CN   102681020 A   9/2012
(Continued)

OTHER PUBLICATIONS

State Intellectual Property Office of the People's Republic of China, Office Action and Search Report Issued in counterpart Chinese Application No. 201810712864.4, dated Aug. 5, 2019, 14 pages-,(Submitted with English-language machine translation).
(Continued)

*Primary Examiner* — Don K Wong
(74) *Attorney, Agent, or Firm* — Fish & Richardson P.C.

(57) ABSTRACT

Methods, devices, systems and apparatus for arranging detector sub-modules in a medical device are provided. In one aspect, a detector includes a housing and a plurality of detector modules arranged in parallel along a direction on the housing and configured to detect rays emitted from a radiation source and attenuated by a subject. Each of the plurality of detector modules includes a support extending in the direction and a plurality of detector sub-modules arranged on the support along the direction. A top surface of each of the plurality of detector sub-modules is tangent to a respective spherical surface of a corresponding target sphere of at least two target spheres having different radiuses, and a respective sphere center of each of the at least two target spheres is substantially overlapped with a focal spot of the radiation source.

20 Claims, 3 Drawing Sheets

(58) Field of Classification Search
CPC ... A61B 6/4208; A61B 6/4014; A61B 6/4266; A61B 6/4411; A61B 6/4275; A61B 6/44; G01N 23/046; G01N 2223/419; G01N 2223/50; G01N 2223/501

See application file for complete search history.

(56) References Cited

U.S. PATENT DOCUMENTS

| | | |
|---|---|---|
| 8,548,119 B2 | 10/2013 | Ikhlef et al. |
| 8,575,555 B2 | 11/2013 | Wangerin et al. |
| 2011/0103544 A1 | 5/2011 | Hermony |
| 2015/0078525 A1 | 3/2015 | Hofmann et al. |
| 2015/0245807 A1 | 9/2015 | Tajima et al. |
| 2016/0170038 A1 | 6/2016 | Yu |
| 2019/0239833 A1 | 8/2019 | Ikhlef |
| 2019/0243006 A1 | 8/2019 | Ikhlef et al. |

FOREIGN PATENT DOCUMENTS

| | | |
|---|---|---|
| CN | 104067112 A | 9/2014 |
| CN | 104287767 A | 1/2015 |
| CN | 105342635 A | 2/2016 |
| CN | 205672033 U | 11/2016 |
| CN | 106255900 A | 12/2016 |
| EP | 1595499 A1 | 11/2005 |
| WO | WO 2010/007544 A1 | 1/2010 |

OTHER PUBLICATIONS

Feng, "The Technology and Application of the Multi-row Detector Used in Multi-slice Spiral CT," The Fifth Issue of China Journal Medical Equipment Information, 2002, 3 pages, Abstract.

\* cited by examiner

DETECTOR MODULE, DETECTOR AND MEDICAL DEVICE

CROSS REFERENCE TO RELATED APPLICATIONS

This application claims priority to Chinese Patent Application No. 201810712864.4 and filed on Jun. 29, 2018, the entire content of which is incorporated herein by reference.

BACKGROUND

The present disclosure relates to the technical field of medical devices and in particular to a detector module, a detector and a medical device.

With continuous development of medical treatment level, more and more medical devices such as a Computed Tomography (CT) device and an angiography machine are used to assist with medical diagnosis or treatment. For example, a CT device may be used to detect a disease of a human body. The CT device may detect X rays penetrating through the human body by a detector and convert received optical signals into electrical signals. A plurality of detector sub-modules mounted on a housing of the detector are used to realize photo-electric conversion. To ensure diagnosis effect of the detector, it is desired to mount more detector sub-modules on the housing of the detector.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, devices, systems and apparatus for arranging detector sub-modules on a housing of a detector of a medical device, e.g., a CT device.

One aspect of the present disclosure features an apparatus for detecting rays emitted from a radiation source and attenuated by a subject, the apparatus including: a support extending in a first direction and a plurality of detector sub-modules arranged on the support along the first direction. A top surface of each of the plurality of detector sub-modules is tangent to a respective spherical surface of a corresponding target sphere of at least two target spheres having different radiuses, and a respective sphere center of each of the at least two target spheres is substantially overlapped with a focal spot of the radiation source.

In some examples, the plurality of detector sub-modules includes first and second detector sub-modules, and the at least two target spheres include first and second target spheres. The first detector sub-module has a first top surface tangent to a first spherical surface of the first target sphere, and the second detector sub-module has a second top surface tangent to a second spherical surface of the second target sphere. The first target sphere has a larger radius than the second target sphere, and a first distance between the first detection sub-module and a midpoint of the support in the first direction is larger than a second distance between the second detection sub-module and the midpoint of the support in the first direction.

The top surface of each of the plurality of detector sub-modules can be tangent to the respective spherical surface of the corresponding target sphere at a center of the top surface.

In some examples, a line connecting a midpoint of the support and the focal spot of the radiation source defines a second direction, and the first direction and the second direction define a plane. For each of the plurality of detector sub-modules, an arc of the top surface of the detector sub-module on the plane can be tangent to a target circle of the corresponding target sphere on the plane at a midpoint of the arc, and a distance between a circle center of the target circle and the focal spot of the radiation source can be less than 1 mm.

The plurality of detector sub-modules can be symmetrically distributed relative to a line connecting a midpoint of the support and the focal spot of the radiation source in the first direction.

Top surfaces of at least two detector sub-modules in the plurality of detector sub-modules can be tangent to respective spherical surfaces of a same target sphere of the at least two target spheres. The at least two detector sub-modules can be symmetrically distributed relative to a line connecting a midpoint of the support and the focal spot in the first direction.

In some implementations, the apparatus includes first protrusions on both ends of a top of the support in the first direction. The top of the support can include a plurality of positioning surfaces between the first protrusions and spaced by second protrusions. Each of the plurality of detector sub-modules can be placed on a respective positioning surface of the plurality of positioning surfaces. The respective positioning surface can be tangent to a corresponding position sphere, and the top surface of the detector sub-module can be tangent to the respective sphere surface of the corresponding target sphere of the at least two target spheres. A sphere center of the corresponding positioning sphere can be substantially overlapped with the focal spot of the radiation source. A difference between a first radius of the corresponding positioning sphere and a second radius of the corresponding target sphere can be substantially identical to a thickness of the detector sub-module along a second direction defined by a line connecting a midpoint of the support and the focal spot of the radiation source.

Another aspect of the present disclosure features a detector including a housing and a plurality of detector modules arranged in parallel along a first direction on the housing and configured to detect rays emitted from a radiation source and attenuated by a subject. Each of the plurality of detector modules includes: a support extending in the first direction and a plurality of detector sub-modules arranged on the support along the first direction. A top surface of each of the plurality of detector sub-modules is tangent to a respective spherical surface of a corresponding target sphere of at least two target spheres having different radiuses, and a respective sphere center of each of the at least two target spheres is substantially overlapped with a focal spot of the radiation source.

In some examples, the plurality of detector sub-modules include first and second detector sub-modules, and the at least two target spheres include first and second target spheres. The first detector sub-module has a first top surface tangent to a first spherical surface of the first target sphere, and the second detector sub-module has a second top surface tangent to a second spherical surface of the second target sphere, and the first target sphere has a larger radius than the second target sphere, and a first distance between the first detection sub-module and a midpoint of the support in the first direction is larger than a second distance between the second detection sub-module and the midpoint of the support in the first direction.

The top surface of each of the detector sub-modules can be tangent to the respective spherical surface at a center of the top surface.

In some cases, a line connecting a midpoint of the support and the focal spot of the radiation source defines a second direction, and the first direction and the second direction define a plane. For each of the plurality of detector sub-modules, an arc of the top surface of the detector sub-module on the plane can be tangent to a target circle of the corresponding target sphere on the plane at a midpoint of the arc, and a distance between a circle center of the target circle and the focal spot of the radiation source can be less than 1 mm.

The plurality of detector sub-modules can be symmetrically distributed relative to a line connecting a midpoint of the support and the focal spot in the first direction.

In some cases, the top surfaces of at least two detector sub-modules in the plurality of detector sub-modules are tangent to respective spherical surfaces of a same target sphere of the at least two target spheres. The at least two detector sub-modules can be symmetrically distributed relative to a line connecting a midpoint of the support and the focal spot in the first direction.

In some implementations, each of the plurality of detector modules further includes first protrusions on both ends of a top of the support in the first direction to cooperate with the housing. The top of the support can include a plurality of positioning surfaces between the first protrusions and spaced by second protrusions. Each of the plurality of detector sub-modules can be placed on a respective positioning surface of the plurality of positioning surfaces. The respective positioning surface can be tangent to a corresponding position sphere, and the top surface of the detector sub-module can be tangent to the respective sphere surface of the corresponding target sphere of the at least two target spheres. A sphere center of the corresponding positioning sphere can be substantially overlapped with the focal spot of the radiation source, and a difference between a first radius of the corresponding positioning sphere and a second radius of the corresponding target sphere can be identical to a thickness of the detector sub-module along a second direction defined by a line connecting a midpoint of the support and the focal spot of the radiation source.

A further aspect of the present disclosure features a medical device including: a scanning gantry including a bore to accommodate a subject, a radiation source configured to emit rays to the subject, a scanning table configured to support the subject, and a detector configured to detect the rays attenuated by the subject and convert the detected rays into electrical signals, the detector and the radiation source being opposite inside the scanning gantry. The detector includes: a housing and a plurality of detector modules arranged in parallel along a first direction on the housing and configured to detect rays emitted from a radiation source and attenuated by a subject.

Each of the plurality of detector modules includes: a support extending in the first direction, and a plurality of detector sub-modules arranged on the support along the first direction. A top surface of each of the plurality of detector sub-modules is tangent to a respective spherical surface of a corresponding target sphere of at least two target spheres having different radiuses, and a respective sphere center of each of the at least two target spheres is substantially overlapped with a focal spot of the radiation source.

The medical device can further include a raster between the subject and the detector. The raster can have a respective raster height for each of the plurality of detector sub-modules, and the respective raster height can depend on a radius of the corresponding target sphere whose spherical surface is tangent to the top surface of the detector sub-module.

The medical device can further include at least one processor and at least one non-transitory machine readable storage medium coupled to the at least one processor having machine-executable instructions stored thereon that, when executed by the at least one processor, cause the at least one processor to perform operations including: receiving raw data generated by the detector, obtaining processed data by correcting noise differences in the raw data based on the different radiuses of the at least two target spheres, and reconstructing an image based on the processed data.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1:
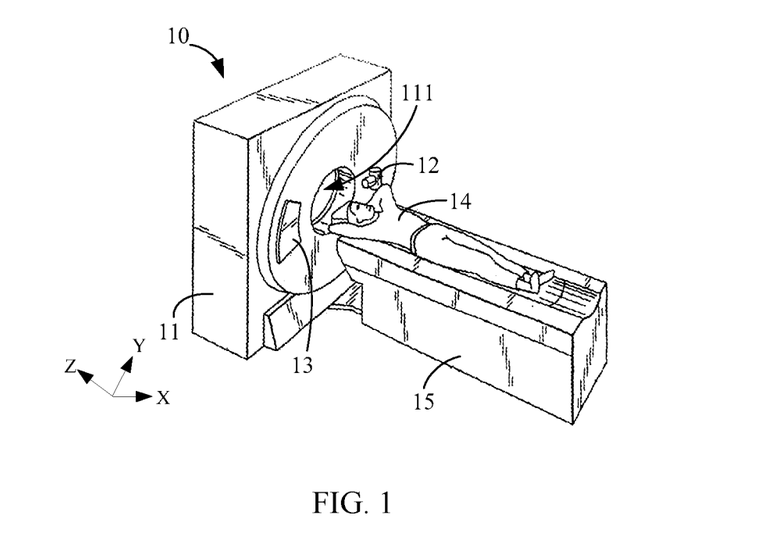
FIG. 1 is a stereoscopic view of a medical device according to one or more examples of the present disclosure.

FIG. 1 is a stereoscopic view of a medical device 10 according to one or more examples of the present disclosure. Descriptions will be made with the medical device 10 as a CT device. The CT device 10 includes a scanning gantry 11, a radiation source 12 and a detector 13. The scanning gantry 11 includes a bore 111 for accommodating a subject 14. The radiation source 12 and the detector 13 are oppositely provided inside the scanning gantry 11. The subject 14, for example, a patient, is placed on a scanning table 15 and may be located in the bore 111 together with the scanning table 15. The radiation source 12 and the detector 13 may rotate relative to the scanning gantry 11 and the subject 14.

The radiation source 12 is configured to emit rays to the subject 14. The radiation source 12 may emit fan-shaped or cone-shaped ray beams, where each ray beam includes a plurality of rays. The radiation source 12 emits the ray beams onto the subject 14 from a focal spot of the radiation source 12. The radiation source 12 may include a ray tube (not shown) and a pressure generator (not shown). The pressure generator provides high voltage electricity to the ray tube and thus the ray tube emits rays. In the example, the rays are X rays.

Figure 2:
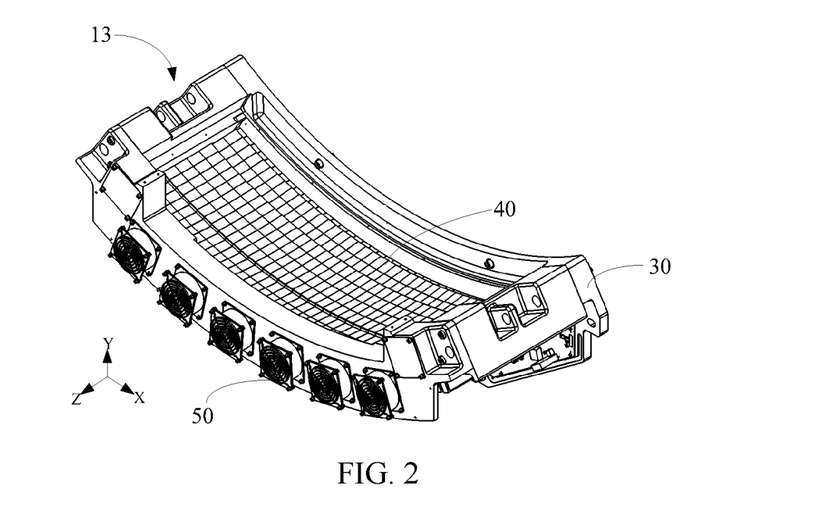
FIG. 2 is a stereoscopic view of a detector of the medical device shown in FIG. 1.

FIG. 2 is a stereoscopic view of a detector 13 according to one or more examples of the present disclosure. The detector 13 includes a housing 30 extending in an arc shape and a plurality of detector modules 40 arranged in parallel on the housing 30. The detector 13 is configured to detect rays attenuated by the subject 14 (hereinafter may also be referred to as attenuated rays) and convert the detected rays into electrical signals. As shown in FIG. 2, each detector module 40 extends in a Z direction in which the subject 14 travels or moves, and is parallel to each other along the Z direction. In the X-Y plane, a plurality of detector modules 40 are arranged in an arc shape, and a circle center of a circle where the arc shape is located is overlapped with the focal spot of the radiation source 12 or near the focal spot. For example, a distance between the circle center of the circle and the focal spot is less than 1 mm, so that rays in the fan-shaped or cone-shaped ray beams emitted by the radiation source 12 may be vertically incident to the detector module 40. The detector 13 may also include a plurality of fans 50 provided on at a side portion of the housing 30. The fans 50 are configured to dissipate heat for the detector 13 to avoid an excessively high temperature when the detector 13 works.

Figure 3:
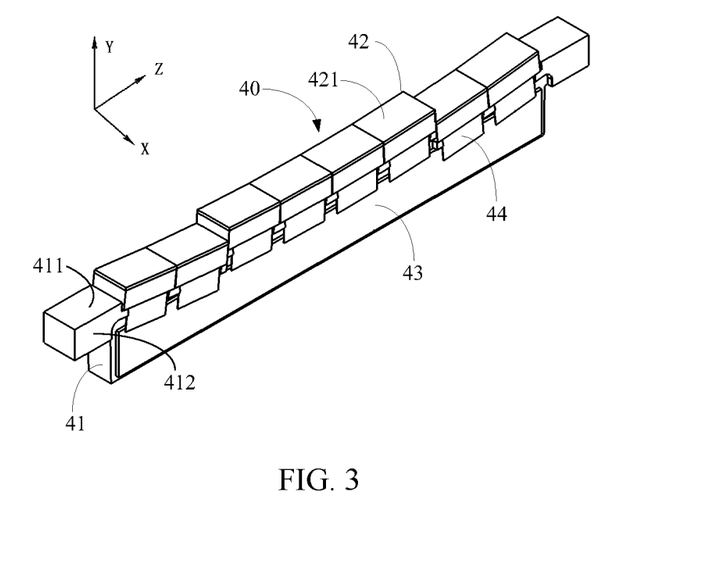
FIG. 3 is a stereoscopic view of a detector module of the detector shown in FIG. 2.
Figure 4:
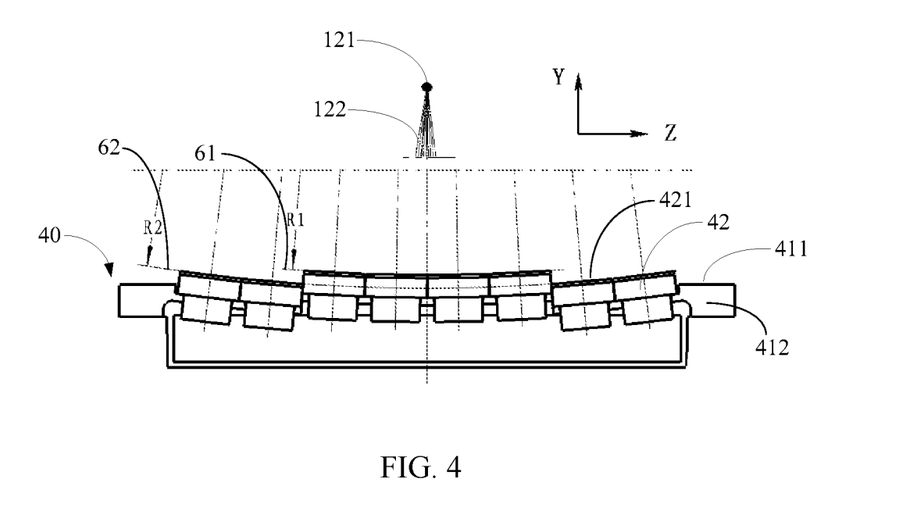
FIG. 4 is a front view of the detector module shown in FIG. 3.

FIG. 3 is a stereoscopic view of a detector module 40 according to one or more examples of the present disclosure. FIG. 4 is a front view of a detector module 40 according to one or more examples of the present disclosure. As shown in FIG. 3 and FIG. 4, the detector module 40 is configured to detect attenuated rays 122. The detector module 40 includes a support 41 extending in the Z direction and a plurality of detector sub-modules 42 arranged on the support 41 in the Z direction.

The detector sub-module 42 is configured to detect the attenuated rays 122 and convert the detected rays into electrical signals. When the rays emitted by the radiation source 12 pass through the subject 14, the rays are attenuated by the subject 14. Because the rays have different attenuation degrees for different tissues and structures in the subject 14, the attenuated rays 122 passing through the subject 14 have different strengths. Optical signals for the attenuated rays 122 are detected and converted into electrical signals by the detector sub-module 42. The strengths of the electrical signals represent strengths of optical signals for the attenuated rays 122. For example, the strengths of electrical signals generated by each detector sub-module 42 can be in direct proportion to the strengths of optical signals for the attenuated rays 122.

In some examples, the detector sub-module 42 includes a scintillator array (not shown), a photodiode (not shown) and a substrate (not shown). The scintillator array is used to detect the attenuated rays 122 and convert the detect rays into visible light. The photodiode is used to obtain electrical signals based on the visible light and the substrate is used to support the scintillator array and the photodiode. The scintillator array may have an array size of 32×16 or 16×16.

In other examples, the detector sub-module 42 includes a cadmium zinc telluride (CZT) crystal, and the CZT crystal is configured to detect the attenuated rays 122 and convert the detected rays into electrical signals.

Figure 5:
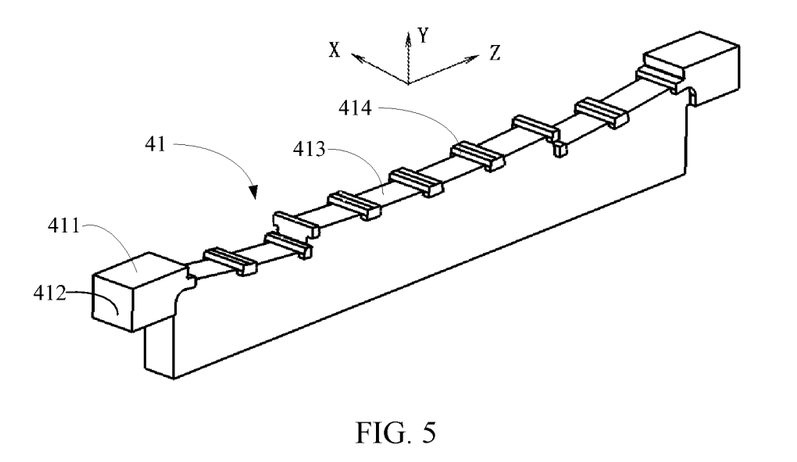
FIG. 5 is a stereoscopic view of a support of the detector module shown in FIG. 3.

The plurality of detector sub-modules 42 are arranged on the support 41 along the Z direction. Each of the plurality of detector sub-modules 42 extends along a direction parallel to a direction where the support 41 extends locally, e.g., a direction where individual positioning surfaces 413 of the support 41 extends (as shown in FIG. 5), so that respective top surfaces on the detector sub-modules 42 to detect the attenuated rays 122 are tangent to spherical surfaces of at least two target spheres. Sphere centers of the at least two target spheres are substantially overlapped with the focal spot 121 of the radiation source 12. The plurality of detector sub-modules 42 are distributed on the spherical surfaces of the at least two target spheres in the Z direction. The at least two target spheres are concentric but different in radius.

FIG. 4 illustrates a structure of the detector module 40 and a positional relationship of the detector module 40 relative to the radiation source 12 in a Y-Z plane as an example. A Y direction is defined by a line connecting the focal spot 121 of the radiation source 12 and a midpoint of the support 41. As shown in FIG. 4, it is assumed that the at least two target spheres respectively correspond to at least two target circles 61, 62 in the Y-Z plane. That is, the orthographic projection of the at least two target spheres in the Y-Z plane is the at least two target circles 61, 62. The top surface of the detector sub-module 42 to detect attenuated rays 122 on the Y-Z plane corresponds to an arc 421 and the arc 421 is substantially located at the circumference of one of the target circles 61, 62. In other words, the arc 421 on the top surface of the detector sub-module 42 is substantially tangent to the corresponding target circle. In addition, since the target spheres are different in radius, the target circles 61, 62 are also different in radius. In this way, rays emitted by the radiation source 12 may be vertically incident at a position where the arc 421 on the top surface of the detector module 40 is tangent to one of the target circles 61, 62. As shown in FIG. 4, the arc 421 on the top surface of the detector sub-module 42 on the Y-Z plane is tangent to the target circle 62, so that rays emitted by the radiation source 12 may be vertically incident at the top surface of the detector sub-module 42. In this way, when electrical signals generated by the detector module 40 are processed subsequently, it is not required or necessary to correct the impact of an angle formed by the attenuated rays 122 and the top surface of the detector sub-module 42 on a ray path, thereby simplifying denoising processing of data.

The arc 421 on the top surface of the detector sub-module 42 on the Y-Z plane is tangent to the corresponding target circles 61, 62 at or near the midpoint of the arc 421. In an example, the arc 421 on the top surface of the detector sub-module 42 on the Y-Z plane is tangent to the target circle 62 at the midpoint of the arc 421, and the distance between the circle center of the corresponding target circle and the focal spot 121 of the radiation source 12 is less than 1 mm. In the example shown in FIG. 4, the arc 421 on the top surface of the detector sub-module 42 on the Y-Z plane is tangent to the corresponding target circle 62 at the midpoint of the arc 421. The rays emitted from the focal spot 121 of the radiation source 12 is vertically incident on the midpoint of the arc 421. The quality of an image reconstructed by the CT device 10 according to projection data converted from electrical signals generated by the detector sub-module 42 is relatively high.

In another example, the arc 421 is tangent to the corresponding target circle 62 near the midpoint of the arc 421. At this case, the circle center of the corresponding target circle is located near the focal spot 121 of the radiation source 12, and rays emitted from the focal spot 121 may be vertically incident near the midpoint of the arc 421 of the detector sub-module 42. When the detector sub-modules 42 are mounted on the support 41, it may be difficult to ensure that the target circle corresponding to each detector sub-module 42 is tangent to the arc 421 of the detector sub-module 42 at the midpoint of arc 421. If the distance between the focal spot 121 and the circle center of the corresponding target circle is within a relatively small deviation range, e.g., less than 1 mm, the impact of the relatively small deviation range on the quality of an image reconstructed based on the electrical signals generated by the detector sub-module 42 can be small. Accordingly, requirements of medical diagnosis can be satisfied. In an example, after the detector sub-module 42 is mounted on the support 41, a distance between the circle center of the target circle tangent to the arc 421 of the detector sub-module 42 and the focal spot 121 of the radiation source 12 is less than 1 mm, and thus it is ensured that the rays emitted from the focal spot 121 of the radiation source 12 are vertically incident at a position near the midpoint of the arc 421, thereby ensuring that the quality of the reconstructed image satisfies the requirements.

A distance between a position of the detector sub-module 42 and the midpoint of the support 41 in the Z direction corresponds to a radius of the target sphere associated with the detector sub-module 42. When the distance is larger, the radius is larger. With reference to FIG. 4, in an example, the radiuses of the plurality of target circles 61, 62 for the detector sub-modules 42 in the Z direction from the midpoint of the support 41 to both ends of the support 41 gradually increase.

If the radius of the target circle corresponding to the detector sub-module 42 is larger, the distance between the arc 421 and the focal spot 121 is larger. For illustrative purpose, FIG. 4 only illustrates eight detector sub-modules 42. However, in a practical application, the number of the detector sub-modules 42 is not limited herein, for example, the number of the detector sub-modules 42 may be 16. In the example shown in FIG. 4, the plurality of detector sub-modules 42 are arranged on positioning surfaces 413 of the support 41 (as shown in FIG. 5) that correspond to the spherical surfaces of the two target spheres. The arcs 421 of the plurality of detector sub-modules 42 are tangent to two target circles 61, 62 with the focal spot 121 as the circle center. The radius R1 of the target circle 61 corresponding to the detector sub-modules 42 near the midpoint of the support 41 is less than the radius R2 of the target circle 62 corresponding to the detector sub-modules 42 on both ends of the support 41. FIG. 4 is merely an illustrative example and the number of the target circles is not limited to the example shown in FIG. 4. In other examples, the arcs 421 of the plurality of detector sub-modules 42 may be tangent to three or more target circles.

In some examples, as shown in FIG. 2, the detector module 40 is formed by splicing a plurality of detector sub-modules 42 with the same cubic in the Z direction. The radiuses of the target circles corresponding to the detector sub-modules 42 from the midpoint of the support 41 to both ends of the support 41 in the Z direction gradually increase, and a width of each of the plurality of detector sub-modules 42 at both ends of the support 41 in the X direction is the same as a width of each of the plurality of detector sub-modules 42 near the midpoint of the support 41 in the X direction. In this case, since a gap between adjacent detector sub-modules 42 in the X direction may be set to be relatively small, scanning data may be effectively collected, thereby improving the quality of the reconstructed image.

In some examples, as shown in FIG. 4, the arcs 421 of at least two detector sub-modules 42 are tangent to the same target circle, that is, the distance between each of the at least two detector sub-modules 42 and the focal spot 121 of the radiation source 12 is the same. Thus, the path travelled by the attenuated rays 122 detected by each of the at least two detector sub-modules 42 is the same. When the electrical signals generated by the plurality of detector sub-modules 42 are corrected, the same correction model is used for the detector sub-modules 42 having the same distance from the focal spot 121 of the radiation source 12. Thus, subsequent data may be processed more easily. In an example, the respective top surfaces of at least two adjacent detector sub-modules 42 are tangent to a spherical surface of the same target sphere. In another example, the respective top surfaces of at least two non-adjacent detector sub-modules 42 are tangent to a spherical surface of the same target sphere. In other examples, at least two adjacent detector sub-modules 42 and at least two non-adjacent detector sub-modules 42 are tangent to a spherical surface of the same target sphere. In the example shown in FIG. 4, the top surfaces of a plurality of adjacent detector sub-modules 42 near the midpoint of the support 41 are tangent to the same target sphere, and the top surfaces of a plurality of detector sub-modules 42 at both ends of the support 41 are tangent to another target sphere. In another example, the top surfaces of the plurality of detector sub-modules near the midpoint of the support 41 may be tangent to a plurality of target spheres with different radiuses and/or the top surfaces of the detector sub-modules 42 at both ends of the support 41 may be tangent to a plurality of target spheres with different radiuses.

In an example, a plurality of detector sub-modules 42 are distributed symmetrically relative to a line connecting the midpoint of the support 41 and the focal spot 121 that is perpendicular to the direction where the support 41 extends, i.e., in the Z direction. The detector sub-modules 42 that are distributed in the Z direction and symmetrically relative to the line connecting the midpoint of the support 41 and the focal spot 121 have the same distance from the focal spot 121 of the radiation source 12. When the rays emitted by the radiation source 12 are incident to the mutually symmetrical detector sub-modules 42, paths travelled by the rays are the same. When the electrical signals generated by the plurality of detector sub-modules 42 are corrected, data differences generated due to different paths travelled by the rays detected by different detector sub-modules 42 need to be corrected. For the detector sub-modules 42 having different distances from the focal spot 121 of the radiation source 12, different correction models are used. For the detector sub-modules 42 having the same distance from the focal spot 121 of the radiation source 12, a same correction model is used. The plurality of detector sub-modules 42 are symmetrically distributed relative to the line connecting the midpoint of the support 41 and the focal spot 121 in the direction where the support 41 extends, such that the data processing may be simplified.

In some examples, the detector module 40 includes one or more analog-digital conversion (ADC) circuits (not shown) and a circuit board 43. As illustrated in FIG. 3, the circuit board 43 can be arranged on a side of the support 41. In some examples, a respective analog-digital conversion (ADC) circuit is integrated onto the substrate of each of the detector sub-modules 42. The analog-digital conversion (ADC) circuit is configured to convert electrical signals into digital signals and send the digital signals to the circuit board 43. The circuit board 43 can be connected to the respective ADC circuits for the detector sub-modules 42. The circuit board 43 is configured to process the digital signals and send the digital signals to a data processing system of the CT device 10. In another example, the ADC circuit is integrated onto the circuit board 43 which is electrically coupled with each of the detector sub-modules 42 through a respective connection line 44. The circuit board 43 is configured to convert electrical signals generated by the detector sub-module 42 into digital signals and send the digital signals to the data processing system of the CT device. In an example, the circuit board 43 is coupled with a power source (not shown) and supplies power to the detector sub-modules 42 through the respective connection lines 44.

FIG. 5 is a stereoscopic view of a support 41 according to one or more examples of the present disclosure. As shown in FIG. 4 and FIG. 5, at least one first positioning surface 411 is formed on the top of the support 41. When the detector module 40 is assembled on the housing 30 of the detector 13, the first positioning surface 411 is cooperated with the housing 30 to fix the detector module 40. In an example, to facilitate assembly of the detector 13 and the housing 30, the at least one first positioning surface 411 is provided at the outermost end of the support 41 in the Z direction. In an example, to tightly connect the detector 13 and the housing 30, the at least one first positioning surface 411 is provided at both ends of the support 41 in the Z direction, respectively. In some examples, two first positioning surfaces 411 located on both ends of the support 41 in the Z direction are arranged symmetrically relative to the midpoint of the support 41. In the example shown in FIG. 5, two protrusion blocks 412 are provided at both ends of the top of the support 41, respectively. The first positioning surfaces 411 refer to top surfaces of the protrusion blocks 412.

A plurality of second positioning surfaces 413 are provided on the top of the support 41 along the Z direction and located between two first positioning surfaces 411. To make sure that the plurality of detector sub-modules 42 may be arranged on the plurality of second positioning surfaces 413 in the above arrangement manner, the second positioning surfaces 413 are distributed onto spherical surfaces of at least two positioning spheres, where the sphere centers of the at least two positioning spheres are substantially overlapped with the focal spot 121 of the radiation source 12. The second positioning surfaces 413 are tangent to the spherical surfaces of the at least two positioning spheres. An arc of the second positioning surface 413 on the Y-Z plane is tangent to a corresponding positioning circle. The positioning circle is an orthographic projection of the positioning sphere on the Y-Z plane. At least two positioning spheres have different radiuses. The radius of the positioning sphere corresponding to the second positioning surface 413 is greater than the radius of the target sphere corresponding to the detector sub-module 42 provided (or arranged) on the second positioning surface 413, and a difference of the two radiuses defines a thickness of the detector sub-module 42 in the Y direction, so that the top surface of the detector sub-module 42 may be tangent to the target sphere after the detector sub-module 42 is fixedly mounted on the support 41.

In some examples, in the Z direction, from the midpoint of the support 41 to both ends of the support 41, a plurality of second positioning surfaces 413 are distributed in the direction in which the support 41 extends and are symmetrically relative to the line connecting the midpoint of the support 41 and the focal spot 121. In some examples, in the Z direction, from the midpoint of the support 41 to both ends of the support 41, the radius of the positioning sphere tangent to the second positioning surface 413 gradually increases. In some examples, both ends of each second positioning surface 413 in the Z direction are provided with a protrusion 414, respectively. That is, the second positioning surface 413 is between two protrusions 414 along the Z direction. When the detector sub-module 42 is mounted on the second positioning surface 413, the detector sub-module 42 is clamped between the protrusions 414 on both ends of the corresponding second positioning surface 413.

With reference to FIGS. 4 and 5, each detector sub-module 42 is provided on the corresponding second positioning surface 413. In some examples, the detector sub-module 42 may be detachably fixedly mounted on the corresponding second positioning surface 413. In some examples, the detector sub-module 42 may be non-detachably fixed on the corresponding second positioning surface 413 through welding, gluing and so on.

Figure 6:
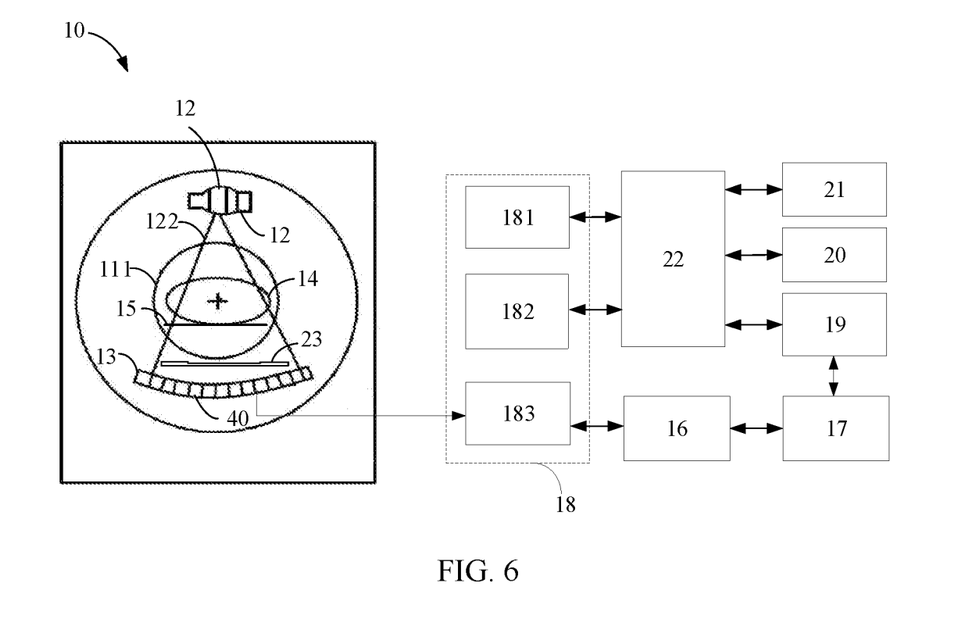
FIG. 6 is a block diagram illustrating the medical device shown in FIG. 1.

FIG. 6 is a block diagram illustrating the CT device 10 shown in FIG. 1. The CT device 10 includes a raster 23 arranged between the subject 14 and the detector module 40. Raster heights for the detector sub-modules 42 corresponding to target spheres with different radiuses are different, that is, the raster height for the detector sub-module 42 depends on the radius of the target sphere tangent to the top surface of the detector sub-module 42. A larger radius corresponds to a larger raster height. The raster 23 is configured to shield scattering of the attenuated rays 122 to be detected by the detector sub-module 42. The attenuated rays 122 to be detected by the detector sub-modules 42 corresponding to target spheres with different radiuses may be scattered to different degrees due to respective different travel paths. Thus, raster heights in the raster 23 are different.

In an example, the CT device 10 includes a controlling module 18 including scanning table controlling unit 181, a scan controlling unit 182 and a data collecting unit 183.

The scanning table controlling unit 181 is configured to control the scanning table 15 to move. The scan controlling unit 182 is configured to control the rotation speeds and angular orientations of the radiation source 12 and the detector 13. The data collecting unit 183 is coupled to the detector 13 to collect digital signals generated by the detector 13 and provide the digital signals (hereinafter may also be referred to as data) to a data processing module 16.

The data processing module 16 is configured to respectively process the data from the detector sub-modules 42 corresponding to target spheres with different radiuses in the same detector module 40. For example, the data processing module 16 is configured to correct data differences caused by the attenuated rays 122 passing through different paths and noise differences in the digital signals based on different radiuses of target spheres. The data processing module 16 is further configured to provide the processed data to an image reconstructing module 17, which is configured to reconstruct an image with the processed data.

The image reconstructed by the image reconstructing module 17 may be stored in a data storage apparatus 19. In an example, the data storage apparatus 19 may store intermediate processing data during an image reconstruction process. In some examples, the data storage apparatus 19 may include, but not limited to, a magnetic storage medium or an optical storage medium, such as a hard disk and a storage chip.

In an example, the CT device 10 may also include an inputting apparatus 20 and a displaying apparatus 21. The inputting apparatus 20 is configured to receive an input from a user and may include a keyboard and/or another user input apparatus. The displaying apparatus 21 may be configured to display a reconstructed image and/or other data. The displaying apparatus 21 may include a liquid crystal display, a cathode-ray tube display and a plasma display and so on.

In an example, the CT device 10 may also include a processor 22. The processor 22 may be configured to receive instructions and scanning parameters and so on that are input through the inputting apparatus 20. The processor 22 may be configured to provide control signals and control information to the scanning table controlling unit 181, the scan controlling unit 182 and the data collecting unit 183.

The data processing module 16, the image reconstructing module 17, the controlling module 18 and the processor 22 of the CT device 10 may be implemented through software and may also be implemented by hardware or a combination of software and hardware. The CT device 10 also includes other components not shown in the drawings. Taking software implementation as an example, the processor 22 is further configured to receive raw data generated by the detector; obtain processed data by correcting noise differences in the raw data based on the different radiuses of the at least two target spheres and reconstruct an image based on the processed data.

The terms used herein are used for the purpose of describing a particular example rather than limiting the present disclosure. Unless otherwise stated, the technical terms or scientific terms used in the present disclosure should have general meanings that are understandable by persons of ordinary skills in the art. Unless otherwise indicated, similar words such as "include" and "contain" are intended to refer to that an element or an object appearing before the word "include" and "contain" cover elements or objects and equivalents listed after the word "include" and "contain" and do not preclude other elements or objects. Similar words such as "connect" and "couple" include physical connections, mechanical connections and electrical connections, directly or indirectly. The singular forms such as "a", 'said", and "the" used in the present disclosure and the appended claims are also intended to include multiple, unless the context clearly indicates otherwise. It is also to be understood that the term "and/or" as used herein refers to any or all possible combinations that include one or more associated listed items.

Examples described in detail herein with the examples thereof expressed in the drawings. When the above descriptions involve the drawings, like numerals in different drawings represent like or similar elements unless stated otherwise. The implementations described in the above examples do not represent all implementations consistent with the present disclosure. On the contrary, they are examples of an apparatus and a method consistent with some aspects of the present disclosure described in detail in the appended claims.

The examples of apparatuses described above are merely illustrative and the units described as separate components may be or not be physically separated, and the components displayed as units may be or not be physical units, i.e., may be located in one place, or may be distributed to a plurality of network units. Part or all of the components may be selected according to actual requirements to implement the objectives of the solutions in the examples.

After considering the specification and practicing the present disclosure, the persons of skill in the prior art may easily conceive of other implementations of the present disclosure. The present disclosure is intended to include any variations, uses and adaptive changes of the present disclosure. These variations, uses and adaptive changes follow the general principle of the present disclosure and include common knowledge or conventional technical means in the prior art not disclosed in the present disclosure. The specification and examples herein are intended to be illustrative only and the real scope and spirit of the present disclosure are indicated by the claims of the present disclosure.

It is to be understood that the present disclosure is not limited to the precise structures described above and shown in the accompanying drawings and may be modified or changed without departing from the scope of the present disclosure. The scope of protection of the present disclosure is limited only by the appended claims.

What is claimed is:

1. An apparatus for detecting rays emitted from a radiation source and attenuated by a subject, the apparatus comprising:
    a support extending in a first direction, a top of the support comprising a plurality of positioning surfaces spaced by a plurality of protrusions along the first direction; and
    a plurality of detector sub-modules arranged on the plurality of positioning surfaces of the support along the first direction, each of the plurality of detector sub-modules being arranged on a respective positioning surface of the plurality of positioning surfaces and being positioned between two respective adjacent protrusions of the plurality of protrusions on both ends of the respective positioning surface along the first direction,
    wherein a top surface of each of the plurality of detector sub-modules is tangent to a respective spherical surface of a corresponding target sphere of at least two target spheres having different radiuses,
    wherein a respective sphere center of each of the at least two target spheres is substantially overlapped with a focal spot of the radiation source,
    wherein a line connecting a midpoint of the support and the focal spot of the radiation source defines a second direction, and the first direction and the second direction define a plane, and
    wherein, for each of the plurality of detector sub-modules, an arc of the top surface of the detector sub-module on the plane is tangent to a target circle of the corresponding target sphere on the plane at a midpoint of the arc, and
    a distance between a circle center of the target circle and the focal spot of the radiation source is less than 1 mm.

2. The apparatus of claim 1, wherein the plurality of detector sub-modules comprises first and second detector sub-modules, and the at least two target spheres comprise first and second target spheres,
    wherein the first detector sub-module has a first top surface tangent to a first spherical surface of the first target sphere, and the second detector sub-module has a second top surface tangent to a second spherical surface of the second target sphere, and
    wherein the first target sphere has a larger radius than the second target sphere, and a first distance between the first detection sub-module and a midpoint of the support in the first direction is larger than a second distance between the second detection sub-module and the midpoint of the support in the first direction.

3. The apparatus of claim 1, wherein each of the plurality of positioning surfaces is tangent to a respective position sphere, and sphere centers of the respective positioning spheres are substantially overlapped with the focal spot of the radiation source, and wherein at least two of the respective position spheres of the plurality of positioning surfaces have different radiuses.

4. The apparatus of claim 3, wherein a line connecting a midpoint of the support and the focal spot of the radiation source defines a second direction, and the first direction and the second direction define a plane, and wherein, for each of the plurality of positioning surfaces, an arc of the positioning surface on the plane is tangent to a corresponding positioning circle that is an orthographic projection of the respective positioning sphere of the positioning surface on the plane.

5. The apparatus of claim 1, wherein top surfaces of at least two detector sub-modules in the plurality of detector sub-modules are tangent to respective spherical surfaces of a same target sphere of the at least two target spheres, and wherein the at least two detector sub-modules are symmetrically distributed relative to a line connecting a midpoint of the support and the focal spot in the first direction.

6. The apparatus of claim 3, wherein the plurality of positioning surfaces and the plurality of protrusions are distributed in the first direction and symmetrical relative to a line connecting a midpoint of the support and the focal spot of the radiation source, and wherein radiuses of the respective position spheres of the plurality of positioning surfaces increase from the midpoint of the support to the ends of the support.

7. The apparatus of claim 1, further comprising:

second protrusions on both ends of the top of the support in the first direction, wherein the plurality of positioning surfaces are between the second protrusions.

8. The apparatus of claim 1, wherein, for each of the plurality of detector sub-modules, the respective positioning surface is tangent to a corresponding position sphere, and the top surface of the detector sub-module is tangent to the respective sphere surface of the corresponding target sphere of the at least two target spheres, and wherein a difference between a first radius of the corresponding positioning sphere and a second radius of the corresponding target sphere is substantially identical to a thickness of the detector sub-module along a second direction defined by a line connecting a midpoint of the support and the focal spot of the radiation source.

9. A detector comprising:

a housing; and a plurality of detector modules arranged in parallel along a first direction on the housing and configured to detect rays emitted from a radiation source and attenuated by a subject, wherein each of the plurality of detector modules comprises:

a support extending in the first direction, a top of the support comprising a plurality of positioning surfaces spaced by a plurality of protrusions along the first direction, and a plurality of detector sub-modules arranged on the plurality of positioning surfaces of the support along the first direction, each of the plurality of detector sub-modules being arranged on a respective positioning surface of the plurality of positioning surfaces and being positioned between two respective adjacent protrusions of the plurality of protrusions on both ends of the respective positioning surface along the first direction, wherein a top surface of each of the plurality of detector sub-modules is tangent to a respective spherical surface of a corresponding target sphere of at least two target spheres having different radiuses, wherein a respective sphere center of each of the at least two target spheres is substantially overlapped with a focal spot of the radiation source, wherein, for each of the plurality of detector sub-modules, the respective positioning surface is tangent to a corresponding position sphere, and the top surface of the detector sub-module is tangent to the respective sphere surface of the corresponding target sphere of the at least two target spheres, and wherein a difference between a first radius of the corresponding positioning sphere and a second radius of the corresponding target sphere is substantially identical to a thickness of the detector sub-module along a second direction defined by a line connecting a midpoint of the support and the focal spot of the radiation source.

10. The detector of claim 9, wherein the plurality of detector sub-modules comprise first and second detector sub-modules, and the at least two target spheres comprise first and second target spheres, wherein the first detector sub-module has a first top surface tangent to a first spherical surface of the first target sphere, and the second detector sub-module has a second top surface tangent to a second spherical surface of the second target sphere, and wherein the first target sphere has a larger radius than the second target sphere, and a first distance between the first detection sub-module and a midpoint of the support in the first direction is larger than a second distance between the second detection sub-module and the midpoint of the support in the first direction.

11. The detector of claim 9, wherein each of the plurality of positioning surfaces is tangent to a respective position sphere, and sphere centers of the respective positioning spheres are substantially overlapped with the focal spot of the radiation source, and wherein at least two of the respective position spheres of the plurality of positioning surfaces have different radiuses.

12. The detector of claim 9, wherein a line connecting a midpoint of the support and the focal spot of the radiation source defines a second direction, and the first direction and the second direction define a plane, and wherein, for each of the plurality of detector sub-modules, an arc of the top surface of the detector sub-module on the plane is tangent to a target circle of the corresponding target sphere on the plane at a midpoint of the arc, and a distance between a circle center of the target circle and the focal spot of the radiation source is less than 1 mm.

13. The detector of claim 11, wherein a line connecting a midpoint of the support and the focal spot of the radiation source defines a second direction, and the first direction and the second direction define a plane, and wherein, for each of the plurality of positioning surfaces, an arc of the positioning surface on the plane is tangent to a corresponding positioning circle that is an orthographic projection of the respective positioning sphere of the positioning surface on the plane.

14. The detector of claim 9, wherein the top surfaces of at least two detector sub-modules in the plurality of detector sub-modules are tangent to respective spherical surfaces of a same target sphere of the at least two target spheres, and wherein the at least two detector sub-modules are symmetrically distributed relative to a line connecting a midpoint of the support and the focal spot in the first direction.

15. The detector of claim 11, wherein the plurality of positioning surfaces are distributed in the first direction and symmetrical relative to a line connecting a midpoint of the support and the focal spot of the radiation source, and wherein radiuses of the respective position spheres of the plurality of positioning surfaces increase from the midpoint of the support to the ends of the support.

16. The detector of claim 9, wherein each of the plurality of detector modules further comprises second protrusions on both ends of the top of the support in the first direction to cooperate with the housing, and wherein the plurality of positioning surfaces are between the second protrusions.

17. A medical device comprising:
a scanning gantry comprising a bore to accommodate a subject;
a radiation source configured to emit rays to the subject;
a scanning table configured to support the subject; and
a detector configured to detect the rays attenuated by the subject and convert the detected rays into electrical signals, the detector and the radiation source being opposite inside the scanning gantry;
wherein the detector comprises:
a housing; and
a plurality of detector modules arranged in parallel along a first direction on the housing and configured to detect rays emitted from a radiation source and attenuated by a subject,
wherein each of the plurality of detector modules comprises:
a support extending in the first direction, a top of the support comprising a plurality of positioning surfaces spaced by a plurality of protrusions along the first direction, and
a plurality of detector sub-modules arranged on the plurality of positioning surfaces of the support along the first direction, each of the plurality of detector sub-modules being arranged on a respective positioning surface of the plurality of positioning surfaces and being positioned between two respective adjacent protrusions of the plurality of protrusions on both ends of the respective positioning surface along the first direction,
wherein a top surface of each of the plurality of detector sub-modules is tangent to a respective spherical surface of a corresponding target sphere of at least two target spheres having different radiuses,
wherein a respective sphere center of each of the at least two target spheres is substantially overlapped with a focal spot of the radiation source,
wherein a line connecting a midpoint of the support and the focal spot of the radiation source defines a second direction, and the first direction and the second direction define a plane, and
wherein, for each of the plurality of detector sub-modules,
an arc of the top surface of the detector sub-module on the plane is tangent to a target circle of the corresponding target sphere on the plane at a midpoint of the arc, and
a distance between a circle center of the target circle and the focal spot of the radiation source is less than 1 mm.

18. The medical device according claim 17, further comprising:
a raster between the subject and the detector,
wherein the raster has a respective raster height for each of the plurality of detector sub-modules, and the respective raster height depends on a radius of the corresponding target sphere whose spherical surface is tangent to the top surface of the detector sub-module.

19. The medical device according claim 17, further comprising:
at least one processor; and
at least one non-transitory machine readable storage medium coupled to the at least one processor having machine-executable instructions stored thereon that, when executed by the at least one processor, cause the at least one processor to perform operations comprising:
receiving raw data generated by the detector;
obtaining processed data by correcting noise differences in the raw data based on the different radiuses of the at least two target spheres; and
reconstructing an image based on the processed data.

20. The medical device according claim 17, wherein, for each of the plurality of detector sub-modules, the respective positioning surface is tangent to a corresponding position sphere, and the top surface of the detector sub-module is tangent to the respective sphere surface of the corresponding target sphere of the at least two target spheres, and
wherein a difference between a first radius of the corresponding positioning sphere and a second radius of the corresponding target sphere is substantially identical to a thickness of the detector sub-module along a second direction defined by a line connecting a midpoint of the support and the focal spot of the radiation source.

* * * * *